May 30, 1961 B. C. SAUR Plant Pat. 2,057
CHRYSANTHEMUM PLANT
Filed July 15, 1960
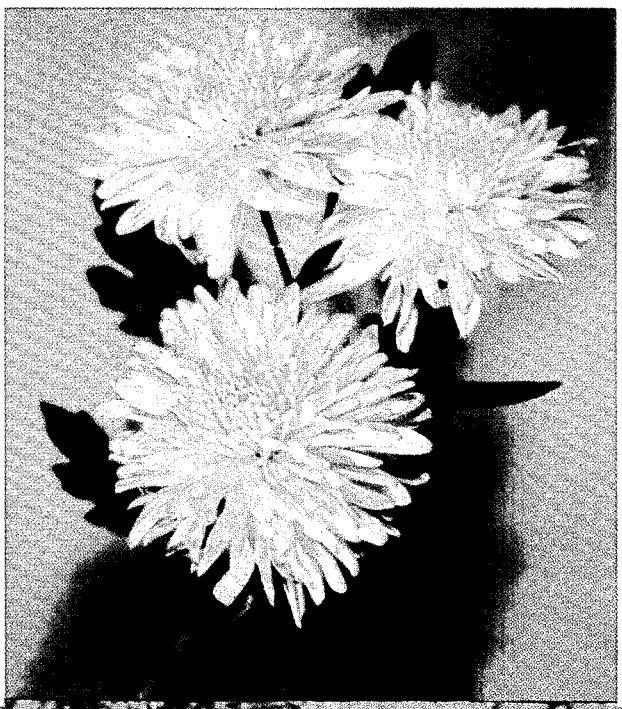
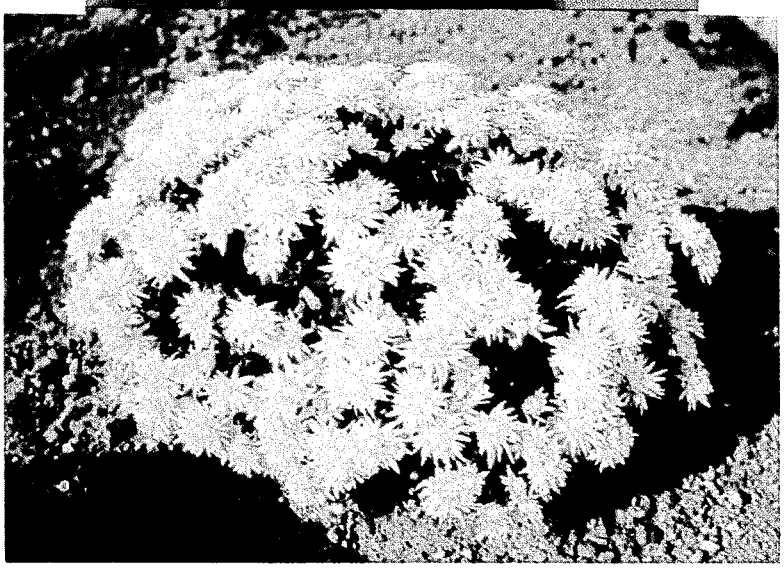
INVENTOR
Belden C. Saur
BY Robb & Robb
ATTORNEYS United States Patent Office Plant Pat. 2,057
Patented May 30, 1961

2,057

CHRYSANTHEMUM PLANT

Belden C. Saur, R.R. 1, Morrow, Ohio

Filed July 15, 1960, Ser. No. 43,256

1 Claim. (Cl. 47—60)

The present invention relates to a new and distinct variety of chrysanthemum plant of the cushion type, which was originated by me by crossing the variety "Lemon Joyous" (unpatented) with the variety "Butter Yellow" (unpatented).

The primary objective of this breeding was to produce a new chrysanthemum variety of the cushion type which bears large flowers. This objective was fully achieved, along with other desirable improvements, as evidenced by the following characteristics which are outstanding in the new variety and which distinguish it from its parents, as well as from all other varieties of which I am aware:

(1) Prolific and early blooming habits;
(2) Persistence and vigor of blooms;
(3) Large flower size and double flower form; and
(4) A distinctive warm apricot general color tonality of the flowers.

Asexual reproduction of my new chrysanthemum variety by cuttings, as performed by me at Morrow, Ohio, shows that the foregoing characteristics and distinctions come true to form and are established and transmitted through succeeding propagations.

The accompanying drawing shows typical specimens of the vegetative growth and flowers of my new chrysanthemum variety in different stages of development, with one view showing a typical plant mound, and another view showing typical specimen flowers on a somewhat enlarged scale, all as depicted in color as nearly true as it is reasonably possible to make the same in a color illustration of this character.

The following is a detailed description of my new variety, with color terminology in accordance with Nickerson Color Fan as published by Munsell Color Company, Inc., of Baltimore, Maryland, except where general color terms of ordinary dictionary significance are obvious, as based upon observations made from specimens grown at Morrow, Ohio:

Parentage: "Lemon Joyous"×"Butter Yellow."

Classification: Cushion.
Growth: Vigorous, healthy mounds.
Cold resistance: Outdoor plants have survived winters at Morrow, Ohio, for several years.
Blooming period: From about September 1 through month of October.

*Flower*

Bud:
*Color.*—When sepals first divide—Strong Reddish Orange, Plate 10R 5/11. When petals begin to unfurl—Strong Yellowish Pink, Plate 10R 7/9. When half-blown: inside of petals—Strong Yellowish Pink, Plate 10R 7/9; outside of petals—Light Orange, Plate 2.5YR 8/6.
*Peduncle.*—Color—Light Orange, Plate 2.5YR 8/6.

Bloom:
*Size.*—About 3 inches in diameter.
*Stem.*—About 4 inches long.
*Form.*—Very double; slightly high-centered.
*Petalage.*—Strap-shaped in at least 10 overlapping rows.
*Color.*—Center of flower—Strong Orange, Plate 2.5YR 6/12. Outer petals—Light Orange, Plate 2.5YR 5/6. Base of petals—Light Yellowish Pink, Plate 2.5YR 9/3. Inside of petals—Moderate Yellowish Pink, Plate 10R 8/6. Reverse of petals—Light Yellowish Pink, Plate 2.5YR 9/3. General tonality—Strong Orange, Plate 2.5YR 7/10.
*Petals.*—Texture—tough; strongly hold form. Form—strap-shaped; rounded on ends.
*Fragrance.*—None.

*Plant*

Form: Cushion type.
Growth: Vigorous; attains height of up to 15 inches; forms perfect rounded mounds both before and while in bloom.

Foliage:
*Size.*—Up to 4 inches long and up to 2 inches wide at widest point.
*Quantity.*—Abundant.
*Color.*—Upper side—Strong Yellowish Green, Plate 10GY 6/9. Under side—Light Yellowish Green, Plate 10GY 8/7.
*Texture.*—Firm and strong.

I claim:

A new and distinct variety of chrysanthemum plant of the cushion type, substantially as herein shown and described, characterized particularly as to novelty by the unique combination of prolific and early blooming habits, persistence and vigor of blooms, large flower size and double flower form, and a distinctive warm apricot general color tonality of the flowers.

No references cited.